United States Patent
Kim et al.

(10) Patent No.: US 11,427,527 B2
(45) Date of Patent: *Aug. 30, 2022

(54) CITRATE-BASED PLASTICIZER AND RESIN COMPOSITION INCLUDING THE SAME

(71) Applicant: LG CHEM, LTD., Seoul (KR)

(72) Inventors: Hyun Kyu Kim, Daejeon (KR); Yun Ki Cho, Daejeon (KR); Joo Ho Kim, Daejeon (KR); Jeong Ju Moon, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/607,070

(22) PCT Filed: May 21, 2018

(86) PCT No.: PCT/KR2018/005789
§ 371 (c)(1),
(2) Date: Oct. 21, 2019

(87) PCT Pub. No.: WO2018/216985
PCT Pub. Date: Nov. 29, 2018

(65) Prior Publication Data
US 2020/0270196 A1 Aug. 27, 2020

(30) Foreign Application Priority Data
May 25, 2017 (KR) .................. 10-2017-0064749

(51) Int. Cl.
*C07C 69/704* (2006.01)
*C08K 5/11* (2006.01)

(52) U.S. Cl.
CPC .............. *C07C 69/704* (2013.01); *C08K 5/11* (2013.01)

(58) Field of Classification Search
CPC .................................. C08K 5/11; C08L 27/06
See application file for complete search history.

(56) References Cited

U.S. PATENT DOCUMENTS

| | | | | |
|---|---|---|---|---|
| 4,009,039 A | * | 2/1977 | Masuda | G03C 1/49845 430/619 |
| 4,587,206 A | | 5/1986 | Sakaguchi et al. | |
| 2002/0198402 A1 | | 12/2002 | Bohnen et al. | |
| 2007/0037926 A1 | | 2/2007 | Olsen et al. | |
| 2011/0046283 A1 | * | 2/2011 | Grass | C07C 69/704 524/285 |
| 2012/0270978 A1 | | 10/2012 | Myers et al. | |
| 2013/0137789 A1 | | 5/2013 | Olsen et al. | |
| 2013/0317152 A1 | * | 11/2013 | Becker | D06N 3/06 524/296 |
| 2017/0081501 A1 | | 3/2017 | Kim et al. | |

FOREIGN PATENT DOCUMENTS

| | | | |
|---|---|---|---|
| CN | 101238175 | 8/2008 | |
| CN | 102633643 | 8/2012 | |
| KR | 10-2002-0085812 | 11/2002 | |
| KR | 10-2012-0109571 | 10/2012 | |
| KR | 10-2016-0047221 | 5/2016 | |
| KR | 10-2016-0134573 | 11/2016 | |
| KR | 10-2017-0020282 | 2/2017 | |
| TW | 201700568 | 1/2017 | |
| WO | WO-2015126391 A1 * | 8/2015 | ............. C07C 67/08 |

* cited by examiner

*Primary Examiner* — John E Uselding
(74) *Attorney, Agent, or Firm* — Dentons US LLP

(57) ABSTRACT

Provided is a citrate-based plasticizer and a resin composition including the same. The citrate-based plasticizer includes one or more citrates having alkyl groups with 7 carbon atoms. The citrate-based plasticizer can solve limitations on migration and volatile loss inherent in the conventional plasticizer and limitations on characteristics of processing such as plasticizing efficiency and absorption rate.

9 Claims, No Drawings

CITRATE-BASED PLASTICIZER AND RESIN COMPOSITION INCLUDING THE SAME

CROSS-REFERENCE TO RELATED APPLICATIONS

The present application is a National Stage Application of International Application No. PCT/KR2018/005789 filed on 21 May 2018, which claims priority to and the benefit of Korean Patent Application No. 10-2017-0064749, filed on 25 May 2017, the entire contents of which are incorporated herein by reference.

TECHNICAL FIELD

The present invention relates to a citrate-based plasticizer and a resin composition including the same.

BACKGROUND ART

Generally, as a plasticizer, an alcohol reacts with a polycarboxylic acid such as phthalic acid and adipic acid to form a corresponding ester. Commercially important examples include adipates of C8, C9 and C10 alcohols, for example, di(2-ethylhexyl) adipate, diisononyl adipate and diisodecyl adipate; and phthalates of C8, C9 and C10 alcohols, for example, di(2-ethylhexyl) phthalate, diisononyl phthalate and diisodecyl phthalate.

Particularly, di(2-ethylhexyl) phthalate is used via plastisol and dry mixing, for the manufacture of toys, films, shoes, paints, flooring materials, gloves, wallpapers, artificial leather, sealant, tarpaulin, automobile floor coatings, furniture, foam mats and acoustical insulation barrier panels, and can be used for exterior décor and insulation of a PVC cable, and for the manufacture of calendered plastic PVC products.

Recently, ester compounds used as a plasticizer include di-(2-ethylhexyl) phthalate (DEHP), di-isononyl phthalate (DINP), di-2-propylheptyl phthalate (DPHP), diisodecyl phthalate (DIDP), etc., but these products are environmental hormones disturbing the endocrine system and harmful to human body, and in addition, according to the use, there are limitations for improving the physical properties of products in view of processability with a resin, absorption rate, volatile loss, migration loss and thermal stability.

Meanwhile, citrates are mostly applied as a secondary plasticizer for improving the physical properties of a common plasticizer. Typically, citrates using C2 to C4 alcohols as raw materials are mostly used. However, due to defects of migration and volatile loss, which are inherent in such products, the citrates are difficult to apply as a sole plasticizer or a primary plasticizer with high content. In addition, if the carbon number of the alcohol raw material is increased to improve the physical properties thereof, adverse effect on plasticizing efficiency, etc. can be anticipated.

In addition, citrates having alkyl groups with different carbon numbers can be used as a sole plasticizer, but in this case, a preparation process is complicated, and the commercialization is difficult due to economic reasons according to the increase of production cost.

Accordingly, development of an eco-friendly or non-phthalate-based compound which can sufficiently improve the physical properties of the conventional products in view of various physical properties such as volatile loss, migration loss and thermal stability as well as processability of a resin, absorption rate, hardness, tensile strength, and elongation rate, is necessary.

DISCLOSURE OF THE INVENTION

Technical Problem

The present invention provides a plasticizer which is applied to a resin composition, has improved physical properties such as plasticizing efficiency, migration resistance and volatile loss, and excellent reproducibility of the physical properties, and provides a citrate-based plasticizer including citrate as a main component and as an eco-friendly material.

Technical Solution

To solve the above-described tasks, according to an embodiment of the present invention, there is provided a citrate-based plasticizer including one or more compounds of the following Formula 1:

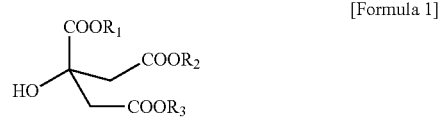

[Formula 1]

In Formula 1, $R_1$ to $R_3$ are each independently an alkyl group having 7 carbon atoms.

To solve the above-described tasks, according to an embodiment of the present invention, there is provided a resin composition including 100 parts by weight of a resin; and 5 to 150 parts by weight of the aforementioned citrate-based plasticizer.

Advantageous Effects

The citrate-based plasticizer according to an embodiment of the present invention, if used in a resin composition, is eco-friendly, has excellent processability due to excellent plasticizing efficiency and appropriate absorption rate, and can provide excellent physical properties such as migration resistance, volatile loss and volatile resistance, and such citrate-based plasticizer can have excellent quality reproducibility.

BEST MODE FOR CARRYING OUT THE INVENTION

Hereinafter, the present invention will be described in more detail in order to assist the understanding of the present invention.

It will be understood that words or terms used in the specification and claims shall not be interpreted as the meaning defined in commonly used dictionaries. It will be further understood that the words or terms should be interpreted as having a meaning that is consistent with their meaning in technical idea of the invention, based on the principle that an inventor can properly define the meaning of the words or terms to best explain the invention.

Citrate-Based Plasticizer

According to an embodiment of the present invention, a citrate-based plasticizer including one or more compounds of Formula 1 below is provided.

[Formula 1]

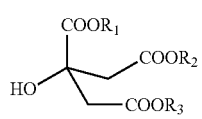

In Formula 1, $R_1$ to $R_3$ are each independently an alkyl group having 7 carbon atoms.

$R_1$ to $R_3$ of Formula 1 can be each independently any one among an n-heptyl group and a 2-methylhexyl group. In the present disclosure, the "2-methylhexyl group" can be commonly referred to as "isoheptyl group" in the art, but is a substituent having a bonded structure of carbon at position of a hexyl group with a methyl group in a chemical structure. However, "TiHC" can be used as English abbreviation, which refers to citrate and can mean triisoheptyl citrate, and can mean a compound of a structure in which a 2-methylhexyl group is bonded to three alkyl substituents of the citrate ($R_1$ to $R_3$ in Formula 1).

Meanwhile, if the citrate is applied as a primary plasticizer, that is, applied as a sole plasticizer or with high content, the citrate, having a low number of carbon atoms, has a small molecular weight and high volatility, and volatile loss or migration are significantly poor. If the carbon number thereof is too large, plasticizing efficiency and absorption rate are not good, and processability can become an issue. In order to supplement this issue, the citrate is commonly applied as a secondary plasticizer.

In addition, citrates in which alkyl groups with different carbon numbers are combined, essentially undergo transesterification reaction, and six (6) kinds of products are prepared. The separation thereof is practically impossible, and a mixture thereof is generally applied for commercialization.

However, the ratio between mixtures can be changed according to the amount of alcohols or reaction conditions, and due to this ratio change, total average molecular weight can be changed or the branch degree of an alkyl group, etc. can be changed and thus, final physical properties may not be the same in all cases and reproducibility can be degraded. Factors for changing physical properties are diverse like this, and if citrates having alkyl groups with different carbon numbers are applied, the quality control of a product and the quality guarantee in all cases are somewhat difficult. If supplementation such as process control to solve these limitations is applied, economic problems including the generation of cost for a separate process can arise.

However, the citrate-based plasticizer according to the present invention includes an alkyl group having 7 carbon atoms, and can have excellent plasticizing efficiency and absorption rate and improve processability to such an extent as to use the citrate as a sole plasticizer, and thus, processability can be improved and migration property and volatile loss can be also equal or improved compared to the conventional plasticizer. In addition, since the number of carbons in the alkyl groups are not different but the same, a plasticizer having excellent reproducibility of product quality can be provided.

In the present disclosure, "non-hybrid citrate" refers to a citrate of which $R_1$ to $R_3$ are all the same alkyl group, and "hybrid citrate" refers to a case where $R_1$ to $R_3$ are different from each other including a case where $R_1$ and $R_2$ are the same but $R_3$ is different, and a case where $R_2$ and $R_3$ are the same but $R_1$ is different.

The citrate-based plasticizer can include one or more selected from compounds of the following Formulae 1-1 to 1-6:

[Formula 1-1]

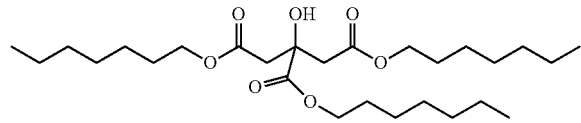

[Formula 1-2]

[Formula 1-3]

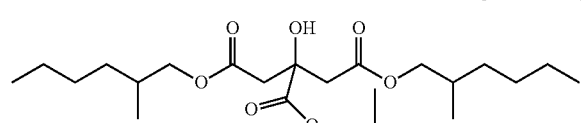

[Formula 1-4]

[Formula 1-5]

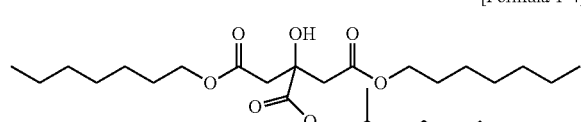

[Formula 1-6]

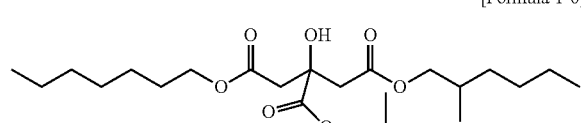

Particularly, the citrate-based plasticizer can be a plasticizer including one kind of a citrate or two kinds of citrates. In this case, the citrate can be a plasticizer including the non-hybrid citrate of Formula 1-1 or the non-hybrid citrate of Formula 1-2, or a plasticizer including both materials.

In addition, the citrate-based plasticizer can include three or more kinds of citrates, and in this case, can be a citrate-based plasticizer including all of Formulae 1-1 to 1-6.

As described above, if the citrate-based plasticizer is used as a sole plasticizer or a primary plasticizer with high content, equivalent degree of plasticizing efficiency (hardness), tensile strength and elongation rate as the phthalate-based compound which is mostly used as the conventional plasticizer, can be obtained and thus, environmental problems can be solved and excellent absorption rate can be attained, thereby becoming a basis of achieving excellent plasticizing efficiency and improving processability. In addition, volatile loss can be decreased, and migration resistance can be significantly excellent.

In addition, the citrate-based compounds can preferably exclude an acetyl citrate in which an acetyl group is bonded instead of hydrogen in a hydroxyl group (—OH). That is, an acetyl group could not be present in a molecule, and a citrate-based compound in which an acetyl group is not bonded can preferably be used. If the acetyl group is present in the citrate-based compound, it is understood that the physical properties of a plasticizer, particularly, processability and gelling property can be degraded due to the deterioration of plasticizing efficiency. Due to limitations including the injection of the plasticizer in an increased amount to overcome the deterioration of the plasticizing efficiency and the cost increase of a product, adverse effects can arise in various aspects including marketability, economic feasibility and physical properties.

Meanwhile, if the citrate-based plasticizer includes three or more kinds of citrates, 3.0 to 99.0 mol % of the non-hybrid citrate of Formula 1-1; 0.5 to 96.5 mol % of a mixture of the first hybrid citrates of Formulae 1-3 and 1-4 with the second hybrid citrates of Formulae 1-5 and 1-6; and 0.5 to 96.5 mol % of the non-hybrid citrate of Formula 1-2 can be included, without limitation.

In case where the citrate-based plasticizer is applied in the aforementioned mixture with a molar ratio in the ranges, the resin composition can be eco-friendly, the processability of a resin can be further improved due to appropriate absorption rate with respect to a resin and short melting time, and physical properties such as hardness, migration loss and volatile loss can be further improved.

Method for Preparing Citrate-Based Plasticizer

According to an embodiment of the present invention, a citrate-based plasticizer can be obtained via direct esterification reaction of citric acid with an alcohol, or via transesterification of a compound of Formula 1 below and an alcohol.

[Formula 1]

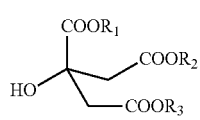

In Formula 1, $R_1$ to $R_3$ are each independently an alkyl group having 7 carbon atoms.

More particularly, in case of preparing a citrate-based plasticizer including the compound of Formula 1-1 or Formula 1-2, direct esterification reaction can be applied, and the direct esterification reaction using citric acid and n-heptyl alcohol or 2-methylhexyl alcohol can be performed. That is, as a method for preparing a non-hybrid citrate, the direct esterification reaction can be performed, and in case of preparing a citrate-based plasticizer including the compound of Formulae 1-1 and 1-2, a method of preparing each and blending thereof can be applied.

The direct esterification reaction can preferably be performed in a temperature range of 80° C. to 270° C., preferably, in a temperature range of 150° C. to 250° C. for 10 minutes to 10 hours, preferably, 30 minutes to 8 hours, more preferably, 1 to 6 hours.

The catalyst of the direct esterification reaction can be an organometallic catalyst including a Sn-based or Ti-based catalyst, an acid catalyst including a sulfonic acid-based or sulfuric acid-based catalyst, or a mixture of catalysts thereof, and the kind of the catalyst is not limited.

The citric acid and the alcohol can preferably be used in an amount of 1:1 to 1:7, preferably, 1:2 to 1:5 in a molar ratio.

By the direct esterification reaction for preparing the citrate, the citrate can be prepared in a yield of about 80% or more.

Particularly, in order to apply a citrate-based plasticizer having a low number of carbon atoms, for example, if butanol is used for applying a citrate-based plasticizer including a butyl group, butanol having a low boiling point is required to be present from the beginning of the reaction as an initial raw material, and due to the low boiling point of butanol, butanol can be evaporated prior to reaching the catalyst activation temperature where esterification reaction is normally performed and may not participate in the reaction but continue circulation in a process. However, in the citrate-based plasticizer according to the present invention, butanol is not required, and the generation of waste water including alcohols having high solubility in water such as butanol can be avoided, and accordingly, secondary energy cost, process cost, etc., can be saved.

In addition, in case of including all compounds of Formulae 1-1 to 1-6 in the citrate-based plasticizer, direct esterification reaction using a mixture of alcohols having 7 carbon atoms can be performed.

The direct esterification reaction using a mixture of alcohols can be more efficient than transesterification. The alcohol with 7 carbon atoms can be a mixture state of alcohols with 7 carbon atoms (can include n-heptanol and 2-methylhexanol as main components and isomers with 7 carbon atoms as subsidiary alcohols) if a separate separation process is not performed, and thus, desired effects can be achieved even though preparing the citrate-based plasticizer according to the present invention by using the mixture of alcohols which has not undergone a separation process. Accordingly, direct esterification reaction using a mixture of alcohols which has not undergone a separate separation process can preferably be applied.

Meanwhile, in addition to the direct esterification reaction, a citrate-based plasticizer can be prepared via transesterification, and transesterification of the non-hybrid citrate of Formula 1-1 or 1-2 with an alcohol having an alkyl group different from the alkyl group of the citrate can be performed.

For example, if the compound of Formula 1-1 is selected as the non-hybrid citrate, the reaction can be performed with 2-methylhexyl alcohol, and if the compound of Formula 1-2 is selected as the non-hybrid citrate, the reaction can be performed with n-heptyl alcohol.

"Transesterification" used in the present disclosure means the reaction of an alcohol and an ester in Reaction 1 below to interchange R' of the alcohol with R" of the ester as shown in Reaction 1 below:

[Reaction 1]

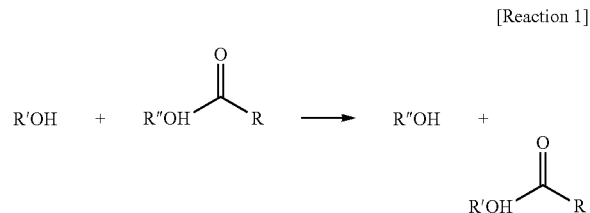

For example, if the alcohol is 2-methylhexyl alcohol, and the citrate is tri(n-heptyl) citrate of Formula 1-1, and if the transesterification is performed, 2-methylhexanoxide of the alcohol can attack all carbonyl carbons of three n-heptyl (RCOOR") groups which are present in the citrate, to form a citrate-based compound of Formula 1-2; can attack the carbonyl carbons of two n-heptyl groups to form the compound of Formula 1-5 or Formula 1-6; or can attack the carbonyl carbon of one n-heptyl (RCOOR") group to form the compound of Formula 1-3 or 1-4; or the compound of Formula 1-1 can remain as an unreacted part of the reaction.

As described above, in case of preparing a citrate-based plasticizer using transesterification, reaction time can be largely decreased.

According to an embodiment of the present invention, the citrate-based plasticizer prepared by the transesterification can include all citrate-based compounds of Formulae 1-1 to 1-6, and the composition ratio of the compounds in the citrate-based composition can be controlled according to the addition amount of an alcohol.

The amount added of the alcohol can be 0.1 to 89.9 parts by weight based on 100 parts by weight, particularly, 3 to 50 parts by weight, more particularly, 5 to 40 parts by weight of the citrate.

If the citrate-based plasticizer is a mixture and includes all citrates of Formula 1-1 to Formula 1-6, the mole fraction of the citrate which is a reactant participating in the transesterification can increase with an increase in the amount of the alcohol, and the amount of a hybrid citrate as a product can increase.

In addition, the amount of citrate present as unreacted material can decrease correspondingly.

According to an embodiment of the present invention, the transesterification can be performed under the reaction temperature of 120° C. to 190° C., preferably, 135° C. to 180° C., more preferably, 141° C. to 179° C. for 10 minutes to 10 hours, preferably, 30 minutes to 8 hours, more preferably, 1 to 6 hours. In the temperature and time ranges, a citrate-based composition with a desired component ratio can be effectively obtained. In this case, the reaction time can be calculated from the point when the reaction temperature is reached after elevating the temperature.

According to an embodiment of the present invention, the transesterification reaction can be performed without a catalyst, or can be performed under an acid catalyst or a metal catalyst, and in this case, the reaction time can be decreased.

The acid catalyst can include, for example, sulfuric acid, methanesulfonic acid or p-toluenesulfonic acid, and the metal catalyst can include, for example, an organometal catalyst, a metal oxide catalyst, a metal salt catalyst, or a metal itself.

The metal component can be, for example, one selected from the group consisting of tin, titanium and zirconium, or a mixture of two or more thereof.

Resin Composition

The present invention provides a resin composition including the citrate-based plasticizer and a resin.

According to an embodiment of the present invention, the resin can be common resin(s) known in the art. For example, one or more selected from the group consisting of ethylene vinyl acetate, polyethylene, polypropylene, polyketone, polyvinyl chloride, polystyrene, polyurethane, thermoplastic elastomer and polylactic acid can be used, without limitation.

The citrate-based plasticizer can be included in an amount of 5 to 150 parts by weight based on 100 parts by weight of the resin.

The resin composition can further include a filler. The amount of the filler can be 0 to 300 parts by weight, preferably, 50 to 200 parts by weight, more preferably, 100 to 200 parts by weight based on 100 parts by weight of the resin.

The filler can be common filler(s), known in the art, without specific limitation. For example, a mixture of one or more selected from silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate and barium sulfate can be used.

The resin composition can further include other additives such as a stabilizer as necessary.

The other additives such as the stabilizer can be included, for example, in an amount of 0 to 20 parts by weight, preferably, 1 to 15 parts by weight based on 100 parts by weight of the resin. The stabilizer can be, for example, a calcium-zinc-based (Ca—Zn-based) stabilizer such as a calcium-zinc composite stearate, without specific limitation.

The citrate-based plasticizer according to an embodiment of the present invention has a short absorption rate with respect to the resin and melting time, and the processability of the resin can be improved, and when prescribing a sheet and a compound of wires, automobile interior materials, films, sheets, tubes, wallpapers, toys, flooring materials, etc., excellent physical properties can be provided.

EXAMPLES

Hereinafter, the present invention will be explained in more detail referring to embodiments. Embodiments according to the present invention can be modified into various other types, and the scope of the present invention should not be limited to the embodiments described below. The embodiments of the present invention are provided for describing the present invention to a person having an average knowledge in the art.

Preparation Example 1: Preparation of tri(n-heptyl) citrate (THC)

To a four-neck, 3 liter reactor equipped with a cooler, a water stripper, a condenser, a decanter, a reflux pump, a temperature controller, and a stirrer, 576 g of separated 2-hydroxypropane-1,2,3-tricarboxlic acid (citric acid), 1,566 g of n-heptyl alcohol (Aldrich) (molar ratio 1:4.5) and 1.44 g (0.25 parts by weight based on 100 parts by weight of citric acid) of a titanium-based catalyst (TnBT, tetra-n-butyl titanate) as a catalyst were injected, followed by slowly elevating the temperature to about 170° C. Around 170° C., water generation was initiated, and esterification reaction was performed for about 4.5 hours while continuously injecting nitrogen gas under the reaction temperature of about 220° C. and an atmospheric pressure. The reaction was finished when an acid value reached 0.1.

After finishing the reaction, distillation extraction was performed for 0.5 to 4 hours under a reduced pressure to remove unreacted raw materials, the reaction product was cooled, and catalyst neutralization treatment was performed. Then, the reaction product was dehydrated to remove water. To the dehydrated reaction product, remaining materials were injected, stirred for a certain time, and filtered to finally obtain 1,431 g (yield: 98%) of tri(n-heptyl) citrate (THC).

Preparation Example 2: Preparation of tri(2-methylhexyl) citrate (TiHC)

The same reaction method as Preparation Example 1 was performed except for using 2-methylhexyl alcohol instead of n-heptyl alcohol in Preparation Example 1 to finally obtain 1,435 g (yield: 98%) of tri(2-methylhexyl) citrate (TiHC).

Preparation Example 3: Preparation of Citrate Mixture (THC-1) of n-heptyl and 2-methylhexyl The same reaction method as Preparation Example 1 was performed except for using n-heptyl alcohol and 2-methylhexyl alcohol at a ratio of 5:5 instead of n-heptyl alcohol of Preparation Example 1. In this case, the citrate mixture was a mixture of 26.5 mol % of the citrate of Formula 1-1, 48.5 mol % of the citrates of Formulae 1-3 and 1-4, and 25.0 mol % of the citrates of Formulae 1-2, 1-5 and 1-6.

Preparation Example 4: Preparation of Citrate Mixture (THC-2) of n-heptyl and 2-methylhexyl By using 1,000 g of a half-finished good THC after extracting for removing unreacted raw materials in Preparation Example 1, and 240 g of a 2-methylhexyl alcohol as reaction materials, transesterification reaction was performed to finally obtain 998 g of a citrate mixture.

In this case, the citrate mixture was a mixture of 54.7 mol % of the citrate of Formula 1-1, 40.5 mol % of the citrates of Formulae 1-3 and 1-4, and 4.8 mol % of the citrates of Formulae 1-2, 1-5 and 1-6.

Comparative Preparation Example 1: Preparation of TBC

By using 384 g of citric acid and 580 g of butanol as reaction raw materials, 706 g (yield: 98%) of tributyl citrate was finally obtained.

Comparative Preparation Example 2: Preparation of TPC

By using 384 g of citric acid and 688 g of 1-pentanol as reaction raw materials, 796 g (yield: 98%) of tripentyl citrate was finally obtained.

Comparative Preparation Example 3: Preparation of THxC

By using 384 g of citric acid and 797 g of n-hexanol as reaction raw materials, 878 g (yield: 98%) of trihexyl citrate was finally obtained.

Comparative Preparation Example 4: Preparation of TOC

By using 384 g of citric acid and 1,014 g of 2-ethylhexanol as reaction raw materials, 1,029 g (yield: 98%) of tri-2-ethylhexyl citrate was finally obtained.

Comparative Preparation Example 5: Preparation of TiNC

By using 384 g of citric acid and 1,123 g of isononanol as reaction raw materials, 1,111 g (yield: 98%) of triisononyl citrate was finally obtained.

Comparative Preparation Example 6: Preparation of BOC253

By using 1,000 g of TOC prepared in Comparative Preparation Example 4 and 300 g of n-butanol as reaction raw materials, transesterification reaction was performed and 840 g of butyloctyl citrate was finally obtained.

The mixture was prepared in molecular weight order from about 20.9 wt % of the sum of three materials including about 2.2 wt % of TBC and about 18.7 wt % of two kinds of citrates of which two 2-ethylhexyl groups were exchanged with butyl groups, which corresponded to about 2 weight ratio, about 45.4 wt % of the sum of two kinds of citrates of which one 2-ethylhexyl group was exchanged with a butyl group, which corresponded to about 5 weight ratio, and about 33.7 wt % of TOC, which corresponded to about 3 weight ratio.

Comparative Preparation Example 7: Preparation of BOC145

By using 1,000 g of TOC prepared in Comparative Preparation Example 4 and 150 g of n-butanol as reaction raw materials, transesterification reaction was performed and 940 g of butyloctyl citrate was finally obtained.

The mixture was prepared in molecular weight order from about 9.9 wt % of the sum of three materials including about 0.7 wt % of TBC and about 9.2 wt % of two kinds of citrates of which two 2-ethylhexyl groups were exchanged with butyl groups, which corresponded to about 1 weight ratio, about 38.9 wt % of the sum of two kinds of citrates of which one 2-ethylhexyl group was exchanged with a butyl group, which corresponded to about 4 weight ratio, and about 51.2 wt % of TOC, which corresponded to about 5 weight ratio.

Examples 1 to 4 and Comparative Examples 1 to 7

The citrates prepared in Preparation Examples 1 to 4 were applied as the plasticizers of Examples 1 to 4, and the citrates prepared in Comparative Examples 1 to 7 were applied as the plasticizers of Comparative Examples 1 to 7. The carbon numbers of the citrates thus applied are summarized in Table 1 below.

TABLE 1

|  | Carbon numbers of citrate alkyl |
| --- | --- |
| Example 1 | 7 |
| Example 2 | 7 |
| Example 3 | 7 |
| Example 4 | 7 |
| Comparative Example 1 | 4 |
| Comparative Example 2 | 5 |
| Comparative Example 3 | 6 |
| Comparative Example 4 | 8 |
| Comparative Example 5 | 9 |
| Comparative Example 6 | 4 and 8 |
| Comparative Example 7 | 4 and 8 |

<Test Items>

Measurement of Hardness

Shore (shore "A") hardness at 25° C., 3T 10 s was measured according to ASTM D2240.

Measurement of Tensile Strength

After pulling at a cross head speed of 200 mm/min (1T) by using a test instrument of U.T.M (manufacturer; Instron, model name; 4466), a position where a specimen was cut was measured according to ASTM D638. The tensile strength was calculated as follows.

Tensile strength (kgf/mm$^2$)=load value (kgf)/thickness (mm)×width (mm)

Measurement of Elongation Rate

After pulling at a cross head speed of 200 mm/min (1T) by using the U.T.M, a position where a specimen was cut was measured according to ASTM D638. The elongation rate was calculated as follows.

Elongation rate (%)=[length after elongation/initial length]×100

Measurement of Migration Loss

A specimen with a thickness of 2 mm or more was obtained, and PS plates were attached on both sides of the specimen and a load of 2 kgf/cm² was applied according to KSM-3156. The specimen was stood in a hot air circulation oven (80° C.) for 72 hours and was taken out and cooled at room temperature for 4 hours. After that, the PS attached to both sides of the specimen were removed, and the weights before and after the standing in the oven were measured. The migration loss was calculated as follows.

Migration loss (%)=[(initial weight of specimen at room temperature weight of specimen after standing in oven)/initial weight of specimen at room temperature]×100

Measurement of Volatile Loss

The specimen thus manufactured was worked at 100° C. for 72 hours, and the weight of the specimen was measured.

Volatile loss (%)=[(weight of initial specimen−weight of specimen after working)/weight of initial specimen]×100

Measurement of Liquid Phase Volatile Loss 40 g of a liquid phase product was put in a vessel with a diameter of 15 centimeters, and stored in a convection oven at 125° C. for 3 hours. The weights before and after this experiment were measured and calculated.

Stress Test

The resin specimen thus manufactured was bent at 180° C. and stored in a chamber of which humidity was fixed to 50% for 72 hours. Then, the specimen was taken out, a folded part was wiped using an oil paper, and the migration degree of a plasticizer was evaluated on a scale of 0-3.

Experimental Example 1: Evaluation of Physical Properties of Resin Specimen

Specimens were manufactured using the plasticizers of Examples 1 to 4 and Comparative Examples 1 to 7.

The specimen was manufactured referring to ASTM D638. With respect to 100 parts by weight of a polyvinyl chloride resin (PVC (LS100S)), 60 parts by weight of one of the citrate-based plasticizers prepared in the examples and the comparative examples, and 3 parts by weight of a stabilizer, BZ153T (Songwon Industrial Co., Ltd.) were blended and mixed at 700 rpm at 98° C. By using a roll mill, working was conducted at 160° C. for 4 minutes, and by using a press, working was conducted at 180° C. for 2.5 minutes (low pressure) and for 2 minutes (high pressure) to manufacture a specimen.

With respect to the specimens, each of the test items were evaluated, and the results are shown in Table 2 below.

TABLE 2

|  | Hardness (Shore A) | Tensile strength (kg/cm²) | Elongation rate (%) | Migration loss (%) | Liquid phase volatile loss (%) | Volatile loss (%) | Stress test (72 hr) |
|---|---|---|---|---|---|---|---|
| Example 1 | 67.5 | 168.5 | 305.8 | 0.39 | 0.03 | 0.86 | 0 |
| Example 2 | 67.2 | 163.6 | 307.4 | 0.40 | 0.04 | 0.93 | 0 |
| Example 3 | 67.3 | 167.9 | 307.0 | 0.38 | 0.03 | 0.88 | 0 |
| Example 4 | 67.4 | 166.5 | 306.2 | 0.40 | 0.03 | 0.90 | 0 |
| Comparative Example 1 | 64.5 | 143.6 | 275.6 | 2.67 | 1.33 | 3.45 | 0.5 |
| Comparative Example 2 | 65.8 | 148.7 | 283.3 | 2.11 | 1.10 | 2.87 | 0.5 |
| Comparative Example 3 | 66.4 | 156.9 | 288.6 | 1.58 | 0.87 | 1.50 | 0.5 |
| Comparative Example 4 | 69.6 | 169.7 | 298.7 | 2.35 | 0.05 | 0.78 | 2.0 |
| Comparative Example 5 | 72.8 | 165.7 | 306.2 | 2.88 | 0.02 | 0.60 | 3.0 |
| Comparative Example 6 | 67.9 | 154.3 | 285.4 | 1.36 | 0.76 | 1.37 | 1.0 |
| Comparative Example 7 | 69.0 | 151.6 | 295.1 | 1.85 | 0.24 | 1.05 | 1.0 |

Referring to Table 2 above, it was determined that Examples 1 to 4 in which citrate-based plasticizers in which an alkyl group having 7 carbon atoms was bonded showed excellent tolerance to stress and markedly decreased migration loss when compared to Comparative Examples 1 to 7. In addition, hardness, tensile strength and elongation characteristic were better than those of the comparative examples, and liquid phase volatile loss was also excellent degree.

Particularly, it was determined that Comparative Examples 1 to 3 in which citrates bonded to an alkyl group having 4 to 6 carbon atoms were applied, showed significantly inferior degree of tensile strength and elongation characteristic when compared to the examples and showed large migration loss and inferior volatile loss. Comparative Examples 4 and 5 in which citrate bonded to an alkyl group having 8 or 9 carbon atoms showed a little high tensile strength or elongation rate but large migration loss and high hardness. Thus, plasticizing efficiency was degraded and tolerance to stress was little, neither. Further, it was determined that better physical properties were not found overall in Comparative Examples 6 and 7 than the examples.

Meanwhile, when comparing Examples 3 and 4 with Comparative Examples 6 and 7, these sets all used a composition in which a hybrid citrate and a non-hybrid citrate were mixed together. As described above, in Examples 3 and 4, the citrates bonded to different substituents within the same carbon number range were used, and the variation range of physical properties was expected to be small and the variation range of overall physical properties was determined to be below 0.5% from the measurement results of physical properties, and it was found that reproducibility was quite excellent. In Comparative Examples 6 and 7, difference of the elongation rate was about 5%, and difference of liquid phase volatile loss was about three times.

Thus, it was found that the achievement of products having equivalent degrees was somewhat difficult.

So if a citrate bonded to an alkyl group having 7 carbon atoms is applied as a plasticizer, it could be determined that the reproducibility of physical properties is excellent, overall physical properties, particularly, tolerance against migration loss and stress might be largely improved, and an excellent plasticizer in view of the balance of overall physical properties without degrading other physical properties might be provided.

Although the exemplary embodiments of the present invention have been described in detail, it is understood that the present invention should not be limited to these exemplary embodiments, but various changes and modifications can be made by one ordinary skilled in the art within the spirit and scope of the present invention as hereinafter claimed.

The invention claimed is:

1. A citrate-based plasticizer comprising:
three or more compounds of the following Formula 1:

[Formula 1]

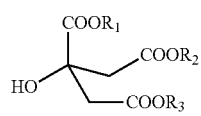

wherein in Formula 1, $R_1$ to $R_3$ are each independently an alkyl group having 7 carbon atoms, and wherein the three or more compounds are different from each other.

2. The citrate-based plasticizer of claim 1, wherein $R_1$ to $R_3$ of Formula 1 are each independently one selected from among an n-heptyl group and a 2-methylhexyl group.

3. The citrate-based plasticizer of claim 1, wherein the three or more compounds are compounds selected from the group consisting of compounds of the following Formulae 1-1 to 1-6:

[Formula 1-1]
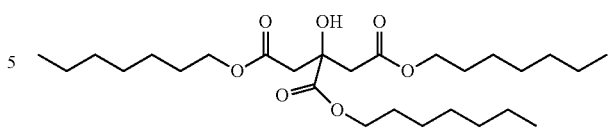

[Formula 1-2]
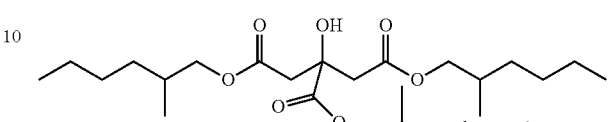

[Formula 1-3]
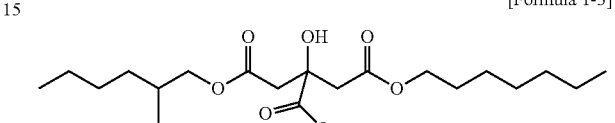

[Formula 1-4]
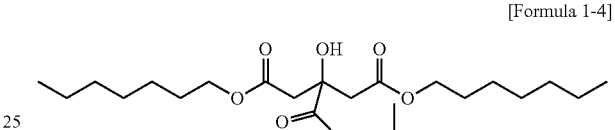

[Formula 1-5]
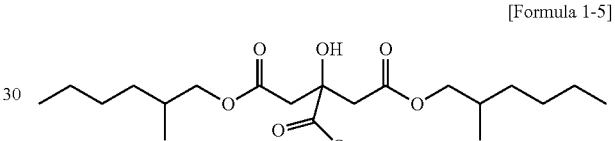

[Formula 1-6]
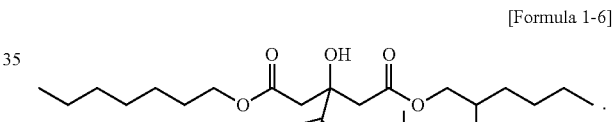

4. The citrate-based plasticizer of claim 1, wherein the three or more compounds of Formula 1 comprises one or more non-hybrid citrates of the following Formula 1-1 and Formula 1-2:

[Formula 1-1]
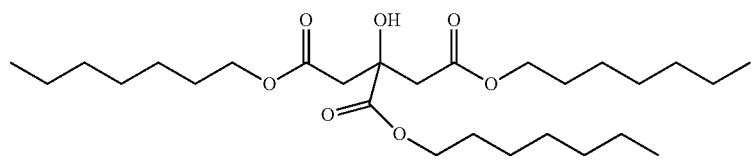

[Formula 1-2]
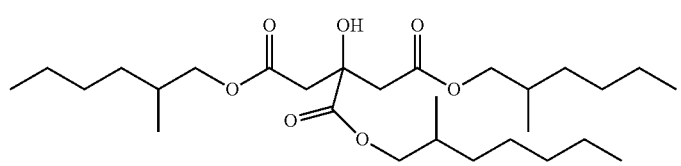

5. A resin composition, comprising 100 parts by weight of a resin and 5 to 150 parts by weight of a citrate-based plasticizer composition, wherein the citrate-based plasticizer composition is the sole plasticizer composition in the resin composition,
wherein the citrate-based plasticizer composition consists of:
non-hybrid citrates of the following Formula 1-1 and Formula 1-2;
first hybrid citrates of the following Formula 1-3 and Formula 1-4; and
second hybrid citrates of the following Formula 1-5 and Formula 1-6:

[Formula 1-1]
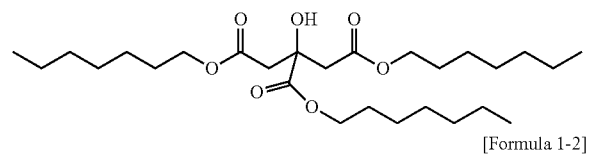

[Formula 1-2]
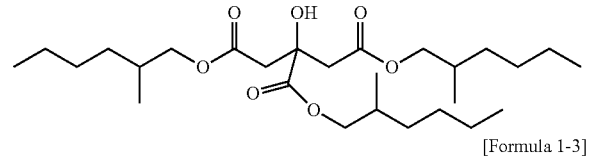

[Formula 1-3]
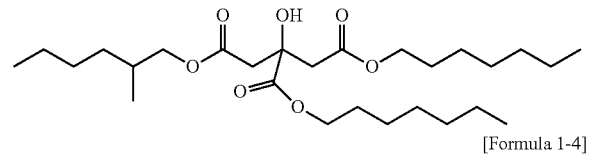

[Formula 1-4]
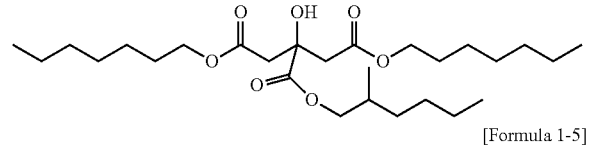

[Formula 1-5]
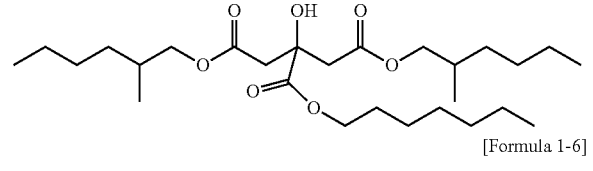

[Formula 1-6]
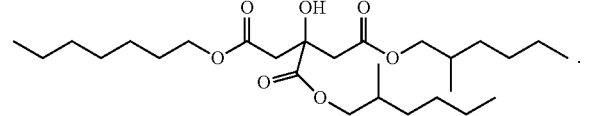

6. The resin composition of claim 5, wherein the resin is one or more selected from the group consisting of ethylene vinyl acetate, polyethylene, polypropylene, polyketone, polyvinyl chloride, polystyrene, polyurethane, and polylactic acid.

7. The citrate-based plasticizer of claim 1, wherein the citrate-based plasticizer comprises:
non-hybrid citrates of the following Formula 1-1 and Formula 1-2;
first hybrid citrates of the following Formula 1-3 and Formula 1-4; and
second hybrid citrates of the following Formula 1-5 and Formula 1-6:

[Formula 1-1]
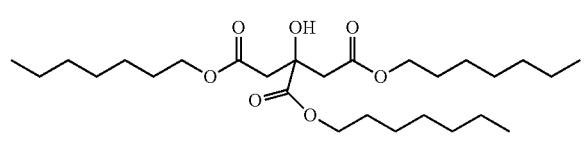

[Formula 1-2]
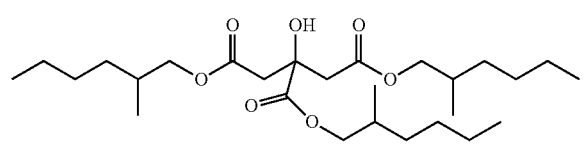

[Formula 1-3]
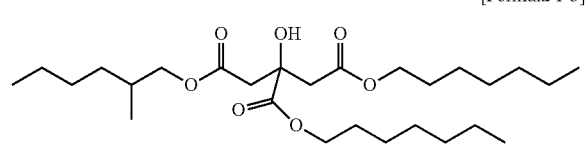

[Formula 1-4]
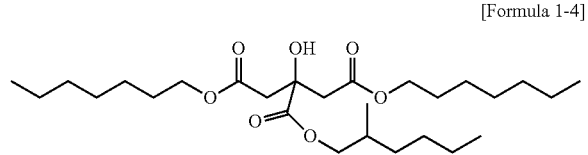

[Formula 1-5]
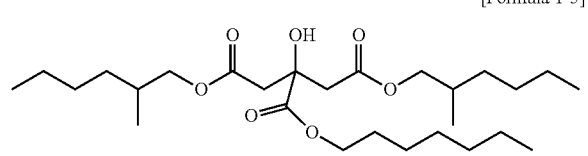

[Formula 1-6]
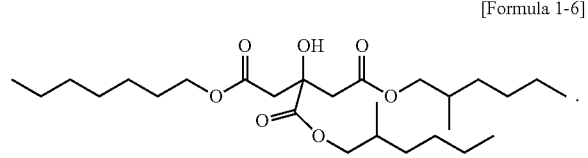

8. A resin composition comprising:
100 parts by weight of a resin, and
5 to 150 parts by weight of the citrate-based plasticizer of claim 1.

9. The resin composition of claim 8, wherein the resin is one or more selected from the group consisting of ethylene vinyl acetate, polyethylene, polypropylene, polyketone, polyvinyl chloride, polystyrene, polyurethane, thermoplastic elastomer and polylactic acid.

* * * * *